United States Patent [19]

Ellis et al.

[11] Patent Number: 5,711,823

[45] Date of Patent: *Jan. 27, 1998

[54] METHOD FOR WETTING CONTACT LENSES

[75] Inventors: Edward J. Ellis; Jeanne Y. Ellis, both of Lynnfield, Mass.

[73] Assignee: Wilmington Partners L.P., Wilmington, Mass.

[*] Notice: The term of this patent shall not extend beyond the expiration date of Pat. No. 5,401,327.

[21] Appl. No.: 391,748

[22] Filed: Feb. 21, 1995

Related U.S. Application Data

[63] Continuation of Ser. No. 80,429, Jun. 18, 1993, Pat. No. 5,401,327.

[51] Int. Cl.$^6$ ................. B08B 3/04; B08B 3/08
[52] U.S. Cl. ................. 134/42; 422/28; 422/34
[58] Field of Search ............ 134/42; 252/174.17, 252/89.1, 106, 174.21, 174.23, 542, 173, 547; 422/28, 34

[56] References Cited

U.S. PATENT DOCUMENTS

| | | | |
|---|---|---|---|
| 3,947,573 | 3/1976 | Rankin | 424/78 |
| 4,168,112 | 9/1979 | Ellis | 351/160 H |
| 4,321,261 | 3/1982 | Ellis et al. | 424/180 |
| 4,323,467 | 4/1982 | Fu | 252/186 |
| 4,324,703 | 4/1982 | Seldner | 252/522 R |
| 4,388,229 | 6/1983 | Fu | 252/549 |
| 4,409,205 | 10/1983 | Shively | 424/78 |
| 4,416,873 | 11/1983 | Puchalski | 424/177 |
| 4,436,730 | 3/1984 | Ellis | 424/180 |
| 4,440,662 | 4/1984 | Tsuzuki | 252/106 |
| 4,482,537 | 11/1984 | El-Menshawy | 424/59 |
| 4,627,973 | 12/1986 | Moran | 424/47 |
| 4,746,674 | 5/1988 | Pierpaoli | 514/415 |
| 4,748,189 | 5/1988 | Su et al. | 514/781 |
| 4,820,352 | 4/1989 | Riedhammer | 134/30 |
| 5,075,400 | 12/1991 | Andrade | 526/307.5 |
| 5,171,264 | 12/1992 | Merrill | 623/3 |
| 5,262,154 | 11/1993 | Wendel | 424/73 |
| 5,275,761 | 1/1994 | Bergmann | 252/551 |
| 5,275,838 | 1/1994 | Merrill | 427/2 |
| 5,292,350 | 3/1994 | Molock | 8/507 |
| 5,326,556 | 7/1994 | Barnet | 424/73 |
| 5,358,667 | 10/1994 | Bergmann | 252/547 |
| 5,401,327 | 3/1995 | Ellis | 134/42 |
| 5,405,878 | 4/1995 | Ellis et al. | 422/28 |

FOREIGN PATENT DOCUMENTS

| | | |
|---|---|---|
| 0079030 | 5/1983 | European Pat. Off. . |
| 0590521 | 4/1994 | European Pat. Off. . |
| 2515201 | 10/1982 | France . |

OTHER PUBLICATIONS

P. Lutz and P. Rempp, *Makromol. Chemie* 189:1051 (1988).
Y. Gnanou, *Makromol. Chemie* 189:2893–2897 (1988).

*Primary Examiner*—Zeinab El-Arini
*Attorney, Agent, or Firm*—Chris P. Konkol; John E. Thomas; Craig E. Larson

[57] ABSTRACT

A method for treating contact lenses with solutions including a material having (a) a hydrophobic core having at least three carbon atoms and (b) at least three hydrophilic polyethylene oxide chains attached to the core.

11 Claims, No Drawings

METHOD FOR WETTING CONTACT LENSES

This is a continuation of application Ser. No. 08/080,429 filed on Jun. 18, 1993, now issued U.S. Pat. No. 5,401,327.

BACKGROUND OF THE INVENTION

1. Field of the Invention

The present invention relates to ophthalmic solutions, particularly to solutions for the treatment of contact lenses. This invention especially relates to solutions for wetting contact lenses.

2. Background

The surfaces of contact lenses must have a certain degree of hydrophilicity to be wet by tears. Tear wettability is in turn necessary to provide the lens wearer with comfort and good vision.

One way to impart wettability to contact lens surfaces is to add hydrophilic monomers to the mixture of comonomers used to form the contact lens material. However, the relative amount of hydrophilic monomer added affects physical properties other than wettability. For example, the hydrophilic monomer content of rigid gas permeable lens materials is much less than that of soft, hydrogel lenses. The rigid lenses accordingly contain only a few percent water of hydration whereas soft lenses contain amounts varying from 10 to 90%. Thus, while hydrophilic monomer addition does increase wettability, the technique is limited by the influence that it has on other properties.

Another way to impart wettability to lens surfaces is to modify the surface after polymerization. For example, surface coatings of hydrophilic polymers have been grated onto the surface. See U.S. Pat. No. 5,171,264. Plasma treatment has also been used to increase the hydrophilicity of hydrophobic surfaces. Although effective, methods such as these are often expensive (requiring complicated and difficult manufacturing procedures) and impermanent.

Water-soluble polymers in lens care solutions have also been used to enhance the wettability of lens surfaces. Use of wetting polymers in this way provides a "cushion" between the lens and the eye which is equated with increased wettability as wearer comfort and tolerance. However, a common drawback with this approach is that the cushion layer dissipates rapidly, since there is little specific interaction between the polymer and the lens surface.

U.S. Pat. Nos. 4,168,112 and 4,321,261 disclose a method to overcome this drawback by immersing the lens in a solution of an oppositely charged ionic polymer to form a thin polyelectrolyte complex on the lens surface. The complex increases the hydrophilic character of the surface for a greater period of time relative to an untreated surface. Of particular interest are cellulosic polymers bearing a cationic charge, said polymers forming a strongly adhered hydrophilic layer on the contact lens surface. These polymers have proven to be exceptional components for wetting, soaking, and lubricating solutions.

While extremely effective for increasing the wettability of the lens, however, it would be desirable to enhance the biocompatibility of the complex formed by cationic cellulosic polymers to increase comfort to the eye.

Polyethylene oxide (PEO) is a unique water-soluble polymer. When in an aqueous environment PEO does not perturb the structure of water and therefore is very "compatible" in a water matrix. Because of these unusual properties PEO has been found to be an effective polymer for low protein adsorptions and low cell adhesion characteristics. However, attempts to employ PEO as a biocompatibilizer in solution have been frustrated by the fact that the low interfacial free energy of PEO/water interfaces results in a very low driving force for adsorption.

PEO coatings on polymeric surfaces have been shown to impart protein resistance and thus improve biocompatibility. Moreover, it has been suggested that a PEO surface on a contact lens would be desirable and methods for grafting PEO to the lens surface have been proposed. However, coating is time consuming and expensive and the coating is usually thin and may be abraded away by handling and/or cleaning.

SUMMARY OF THE INVENTION

We have now found that PEO may be advantageously used in ophthalmic solutions, especially contact lens solutions, and particularly wetting solutions, by employing a PEO component composed of (a) a hydrophobic core having at least three carbon atoms and (b) at least three hydrophilic polyethylene oxide chains attached to the core. The core of these "star-like" components can be "molecular" (glucose is an example) or polymeric (cellulose and styrenics are examples). In either case the core provides a means to achieve a high, localized density of PEO chains. This is highly desirable since protein resistance is a direct function of the length as well as density of PEO chains at an interface.

In a distinct, preferred embodiment of this invention, it has been found that a second surface active polymer component—a cationic cellulosic polymer—may be usefully employed with the star-like component in contact lens solutions. The cationic component complexes with the PEO component and the complex strongly adsorbs on the lens surface. The cationic cellulosic polymer further anchors the PEO on the surface and entangled PEO reaches into the aqueous phase to provide cushioning and protein resistance.

The invention also relates to methods of treating contact lenses using the compositions.

DETAILED DESCRIPTION OF THE INVENTION

The key components in the ophthalmic solutions of this invention are compounds characterized by a hydrophobic core with multiple hydrophilic arms extending therefrom. The "arms" are hydrophilic polyethylene oxide chains, preferably hydroxy-terminated polyethylene oxide chains. The hydrophobic core has at least three carbon atoms, although the precise composition of the core is not otherwise critical to the broader scope of the invention.

These components may be thought of as "star molecules or macromolecules" described by the formula:

$Q(PEO_n)_x$ wherein Q is the hydrophobic core having at least three carbon atoms, PEO represents a hydrophilic (preferably a hydroxy-terminated) radical consisting of repeating —$CH_2CH_2O$— groups, n is the number of ethylene oxide groups in an arm, and x is the number of arms attached to the hydrophobic core.

The length of the arms is not narrowly critical although n is preferably within the range of about 3 to 500, more preferably from about 4 to 100. One advantage of preferred solutions of this invention over solutions containing long, unattached PEO chains is the ability to sterilize the present solutions by autoclaving. A disadvantage of solutions containing long PEO chains is that autoclaving cleaves the chains. Moreover, such solutions are not generally suitable for sterile filtering.

It appears that the enhanced capabilities of PEO components used in the solutions of this invention are related to the ability of the star molecules, when adsorbed on a surface, to concentrate the hydrophilic PEO chains at points across the surface. The core provides hydrophobicity, which in combination with the hydrophilic arms, lends surface activity which in turn leads to surface adsorption. At least three hydrophilic PEO arms are attached to the core, preferably about 4 to 10 arms, more preferably about 4 to about 6 arms. As a general rule, it will be preferable to have many shorter PEO arms attached to a core than to have fewer longer PEO arms attached to a core.

The core contains at least three carbon atoms, although the exact composition of the core is not otherwise narrowly critical to the broad scope of this invention. As the hydrophobicity of core increases, the surface activity of the molecule increases, increasing the surface adsorption of the material. However, it is not desirable for the surface activity of the material to reach the point where detergent-like properties result.

In this connection it should be noted that star molecules employed in this invention do not have hydrophobic arms attached to the core since the presence of the hydrophobic arms would detract from the enhanced properties derived from the hydrophilic PEO arms.

One class of currently preferred star-like components for the solutions of this invention are ethoxylated glucose derivatives. Particularly preferred are polyethylene glycol ethers of methyl glucose conforming generally to the formula:

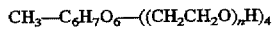

$$CH_3 - C_6H_7O_6 - ((CH_2CH_2O)_nH)_4$$

wherein the ethoxylation value (4n) has an average value within the range of about 10 to 50. Specific examples include methyl gluceth-10 (available from Amerchol Corp., Edison, N.J., as Glucam® E-10) and methyl gluceth-20 (available from Amerchol Corp., Edison, N.J., as Glucam® E-20).

A further class of components for the solutions of this invention are polyethylene oxide star molecules consisting essentially of a plurality of hydroxy-terminated polyethylene oxide chains attached to a divinyl benzene core. Polyethylene oxide star macromolecules of this type have been previously described by Lutz, P. and P. Rempp, Makromol. Chemie 189:1051 (1988) and Gnanou, Y. et al., Makromol. Chemie 189:2893–2897 (1988). Also see U.S. Pat. No. 5,171,264.

These macromolecules are synthesized by anionic polymerization from divinyl benzene (DVB), ethylene oxide and optionally styrene. They have a core of divinyl benzene from which a predetermined number of polyethylene oxide chains or "arms" are grown. The length of each PEO chain corresponds to its molecular weight and typically range from about 1,000 to about 10,000. Preferably, each star molecule will have from about 6 to about 50 arms.

The concentration of hydroxy-termini on the PEO arms can be determined in advance by selection of the gross concentration of star molecules and the number of arms carried by the molecule. For example, a star molecule of 100,000 molecular weight with 20 PEO arms has 20 hydroxyls. To obtain comparable hydroxyl concentrations with linear PEO polymers, the molecular weight would have to be lowered to 10,000. However, hydrogels made of cross-linked linear PEO of comparable molecular weights (MW 10,000) are very fragile.

A still further class of components for the solutions of this invention are ethoxylated derivatives of glycerin. Particularly preferred are polyethylene glycol ethers of glycerin with an average ethoxylation value within the range of about 10 to 50. (Ethoxylation value refers to the total number of ethylene oxide units in the molecule.) A specific example is Glycereth-26 (available from Lonza Inc., Fair Lawn, N.J., as Ethosperse® G-26 and from Lipo Chemicals Inc., Patterson, N.J., as Liponic EG-1).

A still further class of components for the solutions of this invention are ethoxylated derivatives of sorbitol. Particularly preferred are polyethylene glycol ethers of sorbitol having an average ethoxylation value within the range of about 10 to 50. A specific example is Sorbeth-20 (available from Lonza Inc., Fair Lawn, N.J., as Ethosperse® SL-20).

The star-like PEO component may be employed in the compositions at about 0.001 to about 10 weight percent of the composition, preferably at about 0.01 to about 5 weight percent, with about 0.05 to about 3 weight percent being especially preferred.

The solutions of this invention will typically include other components normally found in ophthalmic solutions. However, it has been found particularly advantageous, in a distinct embodiment of this invention, to include a cationic cellulosic material. The cationic component complexes with the PEO component and the complex more strongly adsorbs on the lens surface. The cationic cellulose polymer further anchors the PEO on the surface and entangled PEO reaches into the aqueous phase to provide cushioning and protein resistance.

Any cationic cellulosic material may be used in the practice of this invention. Examples include cellulose polymers containing N,N-dimethyl amino ethyl groups (either protonated or quaternized) and cellulose polymers containing N,N-dimethyl amino-2-hydroxylpropyl groups (either protonated or quaternized).

Cationic cellulosic polymers are commercially available or can be prepared by methods known in the art. As an example, the quaternary nitrogen-containing ethoxylated glucosides can be prepared by reacting hydroxyethyl cellulose with a trimethyl ammonium substituted epoxide. Various preferred cationic cellulosic polymers are commercially available water soluble polymers available under the CTFA (Cosmetic, Toiletry, and Fragrance Association) designation Polyquaternium-10, including the cationic cellulosic polymers available under the tradename UCARE® Polymer from Amerchol Corp., Edison, N.J., USA). These polymers are believed to contain quaternized N,N-dimethyl amino groups along the cellulose polymer chain.

The cationic cellulosic component may be employed in the compositions at about 0.001 to about 10 weight percent of the composition, preferably at about 0.01 to about 5 weight percent, with about 0.05 to about 2 weight percent being especially preferred.

Typical compositions include buffering agents for buffering or adjusting pH of the composition; and/or tonicity adjusting agents for adjusting the tonicity of the composition. Representative buffering agents include: alkali metal salts such as potassium or sodium carbonates, acetates, borates, phosphates, citrates and hydroxides; and weak acids such as acetic, boric and phosphoric acids. Representative tonicity adjusting agents include: sodium and potassium chloride, and those materials listed as buffering agents. The tonicity agents may be employed in an amount effective to adjust the osmotic value of the final composition to a desired value. Generally, the buffering agents and/or tonicity adjusting agents may be included up to about 10 weight percent.

Antimicrobial agents are included in amounts effective to at least inhibit growth of microorganisms in the composition. Preferably, the composition can be used to disinfect a contact lens treated therewith. Various antimicrobial agents are known in the art as useful in contact lens solutions, including: chlorhexidine (1,1'-hexamethylene-bis[5-(p-chlorophenyl) biguanide]) or water-soluble salts thereof, such as chlorhexidine gluconate; polyhexamethylene biguanide (a polymer of hexamethylene biguanide, also referred to as polyaminopropyl biguanide) or water-soluble salts thereof, such as the polyhexamethylene biguanide hydrochloride available under the trade name Cosmocil CQ (ICI Americas Inc.); benzalkonium chloride; and polymeric quaternary ammonium salts. One particularly effective approach to preserving the solutions of this invention is to employ a combination of antibacterial agents combination of chlorhexidine gluconate and polyhexamethylene biguanide hydrochloride has been found to be particularly effective. When present, the antimicrobial agent may be included at 0.00001 to about 5 weight percent, depending on the specific agent.

The compositions may further include a sequestering agent (or chelating agent) which can be present up to about 2.0 weight percent. Examples of preferred sequestering agents include ethylenediaminetetraacetic acid (EDTA) and its salts, with the disodium salt (disodium edetate) being especially preferred.

The star-like components used in the ophthalmic solutions of this invention are very effective at providing the compositions with the ability to wet surfaces of contact lenses treated therewith. If desired, however, the composition may include a supplemental wetting agent. Representative wetting agents include: polyethylene oxide-containing materials (other than the star-like components); cellulosic materials such as cationic cellulosic polymers, hydroxypropyl methylcellulose, hydroxyethyl cellulose, hydroxypropyl cellulose and methylcellulose; polyvinyl alcohols and polyvinyl pyrrolidone. Such additives, when present, may be used in a wide range of concentrations, generally about 0.1 to about 10 weight percent.

The ophthalmic solutions of this invention have humectant properties, providing lubricating and rewetting properties desirable in treating disorders such as dry eye. These humectant properties, coupled with biocompatibility and the ability to repulse protein deposits on lens surfaces, also make the solutions ideal for treating contact lenses.

Contact lenses are treated with the compositions by contacting the lenses with the compositions. For example, a contact lens can be stored in the solution, or soaked in the solution, for sufficient time to wet the surfaces thereof. The treated lens can be inserted directly in the eye, or alternately, the lens can be rinsed. Alternately, drops of solution can be placed on the lens surface and the treated lens inserted in the eye. The specific lens care regimen used will depend on the other compounds present in the solution, as is well known in the art.

For compositions containing an antimicrobial agent, the contact lens is preferably soaked in the composition for sufficient time to disinfect the lens and wet the surface thereof.

The contact lens solutions of this invention are useful for hard, rigid, and soft contact lenses. Hard lenses include polymethylmethacrylate lenses. Rigid gas permeable lenses are generally formed of a silicon or a fluorosilicon polymer. Soft contact lenses include hydrophilic hydrogel lenses.

Specific examples are presented below, but are merely illustrative of the invention and are not meant in any way to limit this invention.

Sample materials for surface analysis were prepared from standard contact lens blanks. Wafers with a diameter of 12.7 mm and a thickness 0.25 mm were cut from the blanks and both surfaces polished to an optical finish using XPAL® (Universal Co.) polishing powder dispersed in deionized water. Polished samples were rinsed thoroughly with deionized water and stored in a clean glass vial under deionized water until use.

Dynamic contact angle measurements were made with hydrated, polished wafers utilizing a Cahn Instruments DCA 322. Wafers were dipped in and out of the test solution 7 times at an average rate of 225 microns per second. All tests were run at room temperature. A computer assisted mathematical analysis of the data yields a graph of contact angle plotted against the vertical position on the wafer. The average advancing and receding contact angles were obtained from the graph.

The surface tension of solution samples is determined with a Cahn Instruments DCA 322. Glass slides measuring 25 mm×30 mm×0.14 mm are flame cleaned and then dipped into the test solution 7 times at an average rate of 225 microns per second. All tests were run at room temperature. A computer assisted mathematical analysis of the data yields a graph of force versus position on the glass slide. The surface tension is obtained from this graph.

The star-like PEO components employed in the following examples are listed below:

Glycereth—26 (CTFA)

Ethoxylated glycerol derivative

Liponic EG-1®

Lipo Chemicals Inc.

Glycereth—26 (CTFA)

Ethoxylated glycerol derivative

Ethosperse G26®

Glyco Chemicals inc.

Sorbeth—20 (CTFA)

Ethoxylated sorbitol derivative

Ethosperse SL-20®

Glyco Chemicals Inc.

Methyl Gluceth—20 (CTFA)

Ethoxylated glucose derivative

Glucam E-20®

Amerchol Corp.

Star macromolecules having divinyl benzene cores with grafted poly(ethylene oxide)

Supplied by MIT

| Sample | MW (total) | MW (arm) | No. Arms |
|--------|-----------|----------|----------|
| 3498 | 363,000 | 10,000 | 36 |
| 3509 | 576,000 | 10,500 | 55 |
| 3510 | 360,000 | 5,200 | 69 |

Controls used in the examples, unless otherwise indicated, are a phosphate buffer system (PBS) having the following composition:

| | |
|---|---|
| Na$_2$HPO$_4$ | 2.80 mg/ml |
| KH$_2$PO$_4$ | 0.55 mg/ml |
| NaCl | 7.80 mg/ml |
| KCl | 1.70 mg/ml |
| Na$_2$EDTA | 0.50 mg/ml |
| PHMB* | 15 ppm |
| WATER | q.s to 1.0 ml |
| PH = | 7.20–7.25 |
| Tonicity = | 350–370 mOsm |

*polyhexamethylene biguanide

EXAMPLE 1

Solutions containing the ingredients shown in Table 1 were prepared and passed through a 0.22 micron sterilizing filter. All solutions were clear and non-viscous.

TABLE 1

| | Solution | | | | | | |
|---|---|---|---|---|---|---|---|
| | 1A | 1B | 1C | 1D | 1E | 1F | 1G |
| Ethosperse G-26, % | | 0.010 | | | | | |
| Ethosperse SL-20, % | | | 0.010 | | | | |
| Glucam E20, % | | | | 0.010 | | | |
| Star #3498, % | | | | | 0.010 | | |
| Star #3509, % | | | | | | 0.010 | |
| Star #3510, % | | | | | | | 0.010 |
| Sodium Phosphate, disbasic % | 0.280 | 0.280 | 0.280 | 0.280 | 0.280 | 0.280 | 0.280 |
| Potassium Phosphate, monobasic % | 0.055 | 0.055 | 0.055 | 0.055 | 0.055 | 0.055 | 0.055 |
| Sodium Chloride % | 0.780 | 0.780 | 0.780 | 0.780 | 0.780 | 0.780 | 0.780 |
| Potassium Chloride % | 0.170 | 0.170 | 0.170 | 0.170 | 0.170 | 0.170 | 0.170 |
| Disodium Edetate % | 0.050 | 0.050 | 0.050 | 0.050 | 0.050 | 0.050 | 0.050 |
| Polyhexamethylene Biguanide, ppm | 15 | 15 | 15 | 15 | 15 | 15 | 15 |
| Deionized Water Q.S. % | 100 | 100 | 100 | 100 | 100 | 100 | 100 |
| Surface Tension (dynes/cm) | 72.5 | 66.8 | 72.0 | 66.5 | 54.9 | 57.9 | 55.5 |

The surface tensions of solutions 1B through 1G are lower than the control solution, 1A without a star PEO components. Samples 1E, 1F and 1G have a PEO star molecule with a strongly hydrophobic core consisting of polymerized divinyl benzene and exhibit markedly lower surface tension among the samples. For this reason it is expected that these PEO star molecules would be more surface active.

EXAMPLE 2

BOSTON RXD® material, a commercial rigid gas permeable fluorosilicone acrylate material, was cut into wafers and both sides polished to an optical finish. Dynamic contact angles (DCA) were determined between the BOSTON RXD and the solutions described in EXAMPLE 1. The results are presented in TABLE 2.

TABLE 2

| Soln | Control 1A | 1B | 1C | 1D | 1E | 1F | 1G |
|---|---|---|---|---|---|---|---|
| S.T. | 72.5 | 66.8 | 72.0 | 66.5 | 54.9 | 57.9 | 55.5 |
| Adv. | 99 | 96 | 97 | 95 | 23 | 33 | 29 |
| Rec. | 31 | 28 | 32 | 40 | 18 | 29 | 25 |
| Adv − Rec | 68 | 68 | 65 | 55 | 5 | 6 | 4 |

S.T. = Surface Tension (dynes/cm)
Adv. = Advancing contact angle in degrees
Rec. = Receding contact angle in degrees
Adv − Rec = Difference between advancing and receding contact angles It is evident that the PEO star molecules range from moderately surface active to strongly surface active when comparing the advancing and receding angles to the control. The effect is most dramatic with the PEO star molecules with the divinyl benzene core, (Samples 1E, 1F and 1G) where both the advancing and receding angles are very close with very little hysteresis (adv.-rec.).

EXAMPLE 3

BOSTON IV® material, a commercial rigid gas permeable silicone acrylate material, was cut into wafers and both sides polished to an optical finish. Dynamic contact angles (DCA) were determined between the BOSTON IV and the solutions described in EXAMPLE 1. The results are presented in TABLE 3.

TABLE 3

| Soln | Control 1A | 1B | 1C | 1D | 1E | 1F | 1G |
|---|---|---|---|---|---|---|---|
| S.T. | 72.5 | 66.8 | 72.0 | 66.5 | 54.9 | 57.9 | 55.5 |
| Adv. | 97 | 93 | 96 | 95 | 20 | 29 | 30 |

TABLE 3-continued

| Soln | Control 1A | 1B | 1C | 1D | 1E | 1F | 1G |
|---|---|---|---|---|---|---|---|
| Rec. | 23 | 19 | 25 | 33 | 17 | 27 | 28 |
| Adv − Rec | 74 | 74 | 71 | 62 | 3 | 2 | 2 |

S.T. = Surface Tension (dynes/cm)
Adv. = Advancing contact angle in degrees
Rec. = Receding contact angle in degrees
Adv − Rec = Difference between advancing and receding contact angles The PEO star molecules tend to lower both the Advancing and the Receding angle and generally lower the difference between the advancing and receding angles (hysteresis). The effect is most pronounced with solution 1E, 1F and 1G as was seen with the fluorosilicone acrylate material, BOSTON RXD.

EXAMPLE 4

FLUOROPERM® 30 material, a commercial rigid gas permeable fluorosilicone acrylate material, was cut into wafers and both sides polished to an optical finish. Dynamic contact angles (DCA) were determined between the FLUOROPERM 30 material and the solutions described in EXAMPLE 1. The results are presented in TABLE 4.

TABLE 4

| Soln | Control 1A | 1B | 1C | 1D | 1E | 1F | 1G |
|---|---|---|---|---|---|---|---|
| S.T. | 72.5 | 66.8 | 72.0 | 66.5 | 54.9 | 57.9 | 55.5 |
| Adv. | 97 | 93 | 95 | 94 | 16 | 26 | 26 |
| Rec. | 23 | 19 | 24 | 34 | 13 | 24 | 25 |
| Adv − Rec | 74 | 74 | 71 | 60 | 3 | 2 | 1 |

S.T. = Surface Tension (dynes/cm)
Adv. = Advancing contact angle in degrees
Rec. = Receding contact angle in degrees
Adv − Rec = Difference between advancing and receding contact angles The PEO star molecules with the more hydrophobic cores (1E, 1F and 1G) dramatically lower the Advancing Contact angle and exhibit very low hysteresis.

EXAMPLE 5

FLUOREX® 700 material, a commercial rigid gas permeable fluorosilicate acrylate material, was cut into wafers and both sides polished to an optical finish. Dynamic contact angles (DCA) were determined between the FLUOREX 700 material and the solutions described in EXAMPLE 1. The results are presented in TABLE 5.

TABLE 5

| Soln | Control 1A | 1B | 1C | 1D | 1E | 1F | 1G |
|---|---|---|---|---|---|---|---|
| S.T. | 72.5 | 66.8 | 72.0 | 66.5 | 54.9 | 57.9 | 55.5 |
| Adv. | 97 | 93 | 95 | 94 | 16 | 29 | 26 |
| Rec. | 23 | 19 | 24 | 34 | 13 | 24 | 25 |
| Adv − Rec | 74 | 74 | 71 | 60 | 3 | 2 | 1 |

S.T. = Surface Tension (dynes/cm)
Adv. = Advancing contact angle in degrees
Rec. = Receding contact angle in degrees
Adv − Rec = Difference between advancing and receding contact angles Similar results were obtained the FLUOREX 700 material as with the other contact lens materials of EXAMPLES 2, 3, 4. It would appear that the PEO star molecules behave similarly on fluorosilicone acrylate, fluorosilicate acrylate and silicone acrylate rigid gas permeable contact lens materials.

EXAMPLE 6

Solutions containing the ingredients shown in Table 6 were prepared and passed through a 0.22 micron sterilizing filter in a clean room environment. The solutions were then packaged in sterile bottles. Physical properties of the solutions are shown in Table 7.

TABLE 6

| Solution | 6A | 6B | 6C | 6D | 6E |
|---|---|---|---|---|---|
| Liponic EG-1, % | 0.300 | — | — | — | — |
| Ethosperse SL-20, % | — | 0.300 | — | — | — |
| Glucam E20, % | — | — | 0.300 | — | — |
| Star #3509, % | — | — | — | 0.300 | — |
| Star #3510, % | — | — | — | — | 0.300 |
| Sodium Phosphate dibasic, % | 0.280 | 0.280 | 0.280 | 0.280 | 0.280 |
| Potassium Phosphate, monobasic, % | 0.055 | 0.055 | 0.055 | 0.055 | 0.055 |
| Sodium Chloride % | 0.700 | 0.700 | 0.700 | 0.700 | 0.700 |
| Potassium Chloride, % | 0.050 | 0.050 | 0.050 | 0.050 | 0.050 |
| Disodium Edetate, % | 0.050 | 0.050 | 0.050 | 0.050 | 0.050 |
| Polyhexamethylene Biguanide, ppm | 15 | 15 | 15 | 15 | 15 |
| Deionized Water Q.S. % | 100 | 100 | 100 | 100 | 100 |

TABLE 7

| | PHYSICAL PROPERTIES | | | | |
|---|---|---|---|---|---|
| Solution | 6A | 6B | 6C | 6D | 6E |
| Viscosity (cps) | 1.8 | 1.5 | 2.2 | 1.4 | 1.5 |
| pH | 7.26 | 7.27 | 7.26 | 7.26 | 7.26 |
| Osmolality (mOsm/kg) | 296 | 301 | 298 | 296 | 294 |
| Surface Tension (dynes/cm) | 46.8 | 46.9 | 47.0 | 49.1 | 48.2 |

EXAMPLE 7

Solutions containing the ingredients shown in Table 8 were prepared to evaluate a star PEO molecule at various concentrations in the presence of a water-soluble ophthalmic polymer. In the solutions, Glucam E-20 was combined with Polymer JR-30M. The Polymer JR-30M, sodium chloride, potassium chloride and disodium edetate were dissolved in deionized water, then autoclaved at 121° C. for 30–40 minutes. The solution was then transferred to a clean room where the remaining ingredients, dissolved in deionized water, were added to the solution through a 0.22 micron filter. The final solutions were mixed and dispensed to sterile bottles. Physical properties of the solutions are shown in Table 9.

TABLE 8

| Solution | 7A | 7B | 7C | 7D |
|---|---|---|---|---|
| Polymer JR-30M, % | 0.100 | 0.100 | 0.100 | 0.100 |
| Glucam E-20, % | — | 0.050 | 0.100 | 0.200 |
| Sodium Phosphate, dibasic, % | 0.280 | 0.280 | 0.280 | 0.280 |
| Potassium Phosphate, monobasic, % | 0.055 | 0.055 | 0.055 | 0.055 |
| Sodium Chloride, % | 0.780 | 0.780 | 0.780 | 0.780 |
| Potassium Chloride, % | 0.170 | 0.170 | 0.170 | 0.170 |
| Disodium Edetate, % | 0.050 | 0.050 | 0.050 | 0.050 |
| Polyhexamethylene Biguanide, % | 15 | 15 | 15 | 15 |
| Deionized Water Q.S., % | 100 | 100 | 100 | 100 |

TABLE 9

| PHYSICAL PROPERTIES | | | | |
|---|---|---|---|---|
| Solution | 7A | 7B | 7C | 7D |
| Viscosity (cps) | 3.0 | 3.1 | 3.3 | 2.9 |
| pH | 7.20 | 7.19 | 7.13 | 7.12 |
| Osmolality (mOsm/kg) | 350 | 347 | 352 | 355 |
| Surface Tension (dynes/cm) | 64.0 | 63.4 | 63.0 | 62.8 |

EXAMPLE 8

The star-like PEO components of this invention were evaluated in combination with a water soluble polymer which is used as an ophthalmic solution component. In this example the PEO components are combined with a cationic cellulosic component, Polymer JR-30M. The JR-30M polymer, sodium chloride, potassium chloride and disodium edetate were dissolved in deionized water. The mixture was then autoclaved at 121 degrees C. for 30–40. minutes. The autoclaved solution was transferred to a clean room where the remaining ingredients, dissolved in deionized water, were added to the solution through a 0.22 micron filter. The final solution was mixed and dispensed to sterile bottles.

Compositions so prepared are described below in Table 10 (all are expressed as weight %, unless otherwise indicated). Physical properties of the compositions are shown in Table 11.

TABLE 10

| Solution | 8A | 8B | 8C |
|---|---|---|---|
| Polymer JR-30M | 0.100 | 0.100 | 0.100 |
| Liponic EG-1 | 0.300 | 0 | 0 |
| Ethosperse SL-20 | 0 | 0.300 | 0 |
| Glucam E-20 | 0 | 0 | 0.300 |
| Sodium Phosphate, dibasic | 0.280 | 0.280 | 0.280 |
| Potassium Phosphate, monobasic | 0.055 | 0.055 | 0.055 |
| Sodium Chloride | 0.780 | 0.780 | 0.780 |
| Potassium Chloride | 0.170 | 0.170 | 0.170 |
| Disodium Edetate | 0.050 | 0.050 | 0.050 |
| Polyhexamethylene Biguanide, ppm | 15 | 15 | 15 |
| Deionized Water, Q.S. | 100 | 100 | 100 |

TABLE 11

| PHYSICAL PROPERTIES | | | |
|---|---|---|---|
| Solution | 8A | 8B | 8C |
| Viscosity (cps) | 3.0 | 3.4 | 3.5 |
| pH | 7.23 | 7.22 | 7.24 |
| Osmolality (mOsm/kg) | 354 | 366 | 364 |
| Surface Tension (dynes/cm) | 61.8 | 62.3 | 60.5 |

EXAMPLE 9

The star-like PEO components of this invention were evaluated in combination with a water soluble polymer which is used as an ophthalmic solution component. In this example the PEO components are combined with a hydroxypropyl methyl cellulose (HPMC) component, Methocel E4M. The HPMC polymer, sodium chloride, potassium chloride and disodium edetate were dissolved in deionized water. The mixture was then autoclaved at 121 degrees C. for 30–40 minutes. The autoclaved solution was transferred to a clean room where the remaining ingredients, dissolved in deionized water, were added to the solution through a 0.22 micron filter. The final solution was mixed and dispensed to sterile bottles.

Compositions so prepared are described below in Table 12 (all are expressed as weight %, unless otherwise indicated). Physical properties of the compositions are shown in Table 13.

TABLE 12

| Solution | 9A | 9B | 9C |
|---|---|---|---|
| Polymer JR-30M | 0.100 | 0.100 | 0.100 |
| Liponic EG-1 | 0.300 | 0 | 0 |
| Ethosperse SL-20 | 0 | 0.300 | 0 |
| Glucam E-20 | 0 | 0 | 0.300 |
| Sodium Phosphate, dibasic | 0.280 | 0.280 | 0.280 |
| Potassium Phosphate, monobasic | 0.055 | 0.055 | 0.055 |
| Sodium Chloride | 0.780 | 0.780 | 0.780 |
| Potassium Chloride | 0.170 | 0.170 | 0.170 |
| Disodium Edetate | 0.050 | 0.050 | 0.050 |
| Polyhexamethylene Biguanide, ppm | 15 | 15 | 15 |
| Deionized Water Q.S. | 100 | 100 | 100 |

TABLE 13

| PHYSICAL PROPERTIES | | | |
|---|---|---|---|
| Solution | 9A | 9B | 9C |
| Viscosity (cps) | 2.5 | 2.3 | 2.3 |
| pH | 7.16 | 7.20 | 7.23 |
| Osmolality (mOsm/kg) | 355 | 368 | 356 |
| Surface Tension (dynes/cm) | 53.3 | 49.9 | 56.5 |

EXAMPLE 10

The solutions prepared in Example 6 were evaluated on eye to assess the clinical suitability of star-like PEO compounds as a contact lens solution component. Clean BOSTON RXD lenses for two adapted RGP lens wearers were soaked in the solutions overnight. Each subject installed the lenses directly from the solution (no rinsing step) and was examined immediately by a clinician who evaluated a number of parameters using a biomicroscope.

All solutions provided a conditioned lens surface which was 100% wet by the tear film. All solutions provided a conditioned lens surface which supported a very even tear film layer. The subjects found the solutions to be compatible with the ocular environment and provide a smooth feel. Tear break-up times (TBUT) are shown below in Table 14.

TABLE 14

| SOLUTION | TBUT (sec.) |
|---|---|
| 6A | 4–7 |
| 6B | 6–11 |
| 6C | 6–11 |
| 6D | 6–11 |
| 6E | 7–15 |

EXAMPLE 11

The solutions prepared in Example 7 were evaluated on eye to assess the clinical suitability of star-like PEO compounds in combination with a cationic cellulose polymer in a contact lens solution base. Clean BOSTON RXD lenses for two adapted RGP lens wearers were soaked in the solutions overnight. Each subject installed the lenses directly from the solution (no rinsing step) and was examined immediately by a clinician who evaluated a number of parameters using a biomicroscope.

All solutions provided a conditioned lens surface which was 100% wet by the tear film. All solutions except Solution 7A provided a conditioned lens surface which supported a very even tear film layer. Solution 7A exhibited some thin spots in the tear film. The solutions containing a star-like PEO component (GLUCAM E-20) provided a more even tear film than the control solution (7A). The subjects reported that the solutions of this invention provided a degree of comfort when inserting the lenses. Tear break-up times (TBUT) are shown below in Table 15.

TABLE 15

| SOLUTION | TBUT (sec.) |
|---|---|
| 7A | 4–9 |
| 7B | 4–15 |
| 7C | 5–10 |
| 7D | 6–10 |

EXAMPLE 12

The solutions prepared in Example 8 were evaluated on eye to assess the clinical suitability of star-like PEO compounds in combination with a cationic cellulose polymer in a contact lens solution base. Clean BOSTON RXD lenses for two adapted RGP lens wearers were soaked in the solutions overnight. Each subject installed the lenses directly from the solution (no rinsing step) and was examined immediately by a clinician who evaluated a number of parameters using a biomicroscope.

All solutions provided a conditioned lens surface which was 100% wet by the tear film. All solutions provided a conditioned lens surface which supported a very even tear film layer. Tear break-up times (TBUT) are shown below in Table 16.

TABLE 16

| SOLUTION | TBUT (sec.) |
|---|---|
| 8A | 5–13 |
| 8B | 7–15 |
| 8C | 6–13 |

This example illustrates the versatile nature of the star-like PEO components in providing an even, wetting tear film layer on the contact lens surface. Tear break-up times ranged from moderate to high which indicates the tenacity of the tear film layer.

EXAMPLE 13

The solutions prepared in Example 9 were evaluated on eye to assess the clinical suitability of various star-like PEO compounds in combination with hydroxypropyl methylcellulose, a commonly used ophthalmic solution ingredient. Clean BOSTON RXD lenses for two adapted RGP lens wearers were soaked in the solutions overnight. Each subject installed the lenses directly from the solution (no rinsing step) and was examined immediately by a clinician who evaluated a number of parameters using a biomicroscope.

All solutions provided a conditioned lens surface which was 100% wet by the tear film. All solutions provided a conditioned lens surface which supported a very even tear film layer. The subjects found the solutions to provide a smooth feeling and minimum discomfort when inserting the lenses. Tear break-up times (TBUT) are shown below in Table 17.

TABLE 17

| SOLUTION | TBUT (sec.) |
|---|---|
| 9A | 5–13 |
| 9B | 7–15 |
| 9C | 6–13 |

EXAMPLE 14

A prototype RGP lens conditioning solution containing a star-like PEO component was prepared. All ingredients, with the exception of the GLUCAM E-20 and the polyhexamethylene biguanide were dissolved in deionized water. The mixture was then autoclaved at 121 degrees C. for 30–40 minutes. The solution was allowed to cool to 30–40 degrees C. before GLUCAM E-20 was added through a sterile 0.22 micron filter. The batch was thoroughly mixed and dispensed to sterile bottles in a clean room environment.

The composition so prepared is described below in Table 18 (all ingredients are expressed as weight %, unless otherwise indicated). Physical properties of the compositions are shown in Table 19.

TABLE 18

| INGREDIENTS | 14A |
|---|---|
| Methocel E-4M | 0.500 |
| Polymer JR-30M | 0.100 |
| Glucam E-20 | 0.020 |
| Sodium Borate | 0.080 |
| Boric Acid | 0.500 |

TABLE 18-continued

| INGREDIENTS | 14A |
|---|---|
| Sodium Chloride | 0.780 |
| Potassium Chloride | 0.170 |
| Disodium Edetate | 0.050 |
| Polyhexamethylene Biguanide, ppm | 15 |
| Deionized Water Q.S. | 100 |

TABLE 19

| PHYSICAL PROPERTIES | 14A |
|---|---|
| Viscosity (cps) | 3.5 |
| pH | 7.1 |
| Osmolality (mOsm/kg) | 455 |
| Surface Tension (dynes/cm) | 50.5 |

EXAMPLE 15

The solution described in Example 14 was evaluated on-eye to assess its compatibility with the ocular environment. Eleven non-contact lens wearers participated in the study. Each subject was examined with a biomicroscope prior to being dispensed Solution 14A to establish the baseline condition of the subjects' eyes. Each subject was instructed to put one or two drops of solution 14A directly into the eye on an hourly basis on each study day. After four hours (i.e., after five administrations of the drops) each subject was re-examined by the clinician, who compared the condition of the eye to that at baseline. Each subject was also questioned about his/her impressions of the comfort or feel of Solution 14A.

The subjects repeated, on average, 6.3 days of evaluation with a range from a minimum of 5 days to a maximum of 8 days. The total number of administrations of solution 14A was 345.

No adverse responses were found. There were no signs of irritation to the cornea in terms of ulceration, opacity, or decrease in luster, and there were no signs of redness or swelling of the conjunctiva, as defined by the Modified Draize Grades for Ocular Lesions in *U.S. Food and Drug Administration 1965 Illustrated Guide for Grading Eye Irritation by Hazardous Substances*, U.S. Government Printing Office, Washington, D.C.

None of the subjects reported specific symptoms or general feelings of discomfort at baseline or at four hours. There were no clinically detectable signs or symptoms of ocular irritation.

We claim:

1. A method for wetting contact lenses which comprises the step of contacting a lens with an aqueous solution comprising a material composed of (a) a hydrophobic core having at least three carbon atoms and (b) at least three hydrophilic polyethylene oxide chains attached to the core, wherein the core excludes hydrophobic arms attached thereto.

2. The method of claim 1 wherein said material is an ethoxylated glucose derivative.

3. The method of claim 2 wherein the ethoxylated glucose derivative is a polyethylene glycol ether of methyl glucose.

4. The method of claim 1 wherein said material is a polyethylene oxide star molecule consisting essentially of a plurality of hydroxy-terminated polyethylene oxide chains attached to a divinyl benzene core.

5. The method of claim 1 wherein said material is an ethoxylated derivative of glycerin.

6. The method of claim 1 wherein said material is an ethoxylated derivative of sorbitol.

7. The method of claim 1 wherein the solution further comprises a cationic cellulosic polymer.

8. The method of claim 1, wherein the step of contacting the lens with the solution consists of soaking the lens in the solution.

9. The method of claim 8, wherein said soaking is followed by inserting the lens directly into the eye.

10. The method of claim 1, wherein the step of contacting the lens with the solution consists of placing drops of the solution on a surface of the lens.

11. The method of claim 10, wherein the step of placing drops of the solution on the surface of the lens is followed by inserting the lens directly into an eye.

* * * * *